United States Patent
Andreiko et al.

(10) Patent No.: US 6,190,165 B1
(45) Date of Patent: Feb. 20, 2001

(54) PLASTIC ORTHODONTIC APPLIANCE HAVING MECHANICAL BONDING BASE AND METHOD OF MAKING SAME

(75) Inventors: Craig A. Andreiko, Alta Loma; Thomas V. Selkee, Claremont, both of CA (US)

(73) Assignee: Ormco Corporation, Orange, CA (US)

( * ) Notice: Under 35 U.S.C. 154(b), the term of this patent shall be extended for 0 days.

(21) Appl. No.: 09/273,649

(22) Filed: Mar. 23, 1999

(51) Int. Cl.⁷ ............................................. A61C 3/00
(52) U.S. Cl. ................................................. 433/9
(58) Field of Search ............................... 433/8, 9

(56) References Cited

U.S. PATENT DOCUMENTS

| | | |
|---|---|---|
| 5,295,823 | 3/1994 | Farzin-Nia ........................... 433/9 |
| 5,522,725 | 6/1996 | Jordan et al. ....................... 433/9 |
| 5,622,494 | 4/1997 | Andreiko et al. ................... 433/9 |

*Primary Examiner*—John J. Wilson
(74) *Attorney, Agent, or Firm*—Wood, Herron & Evans, L.L.P.

(57) ABSTRACT

This invention is directed to a plastic orthodontic appliance having projections extending outwardly from a bonding base. The projections include broadened outer extremities and undercuts proximate the outer extremities which form mechanical bonds with a bonding adhesive. The projections have peened free ends that form the undercuts, preferably with minute fractures therein extending into the outer extremities of the projections. In one application, a plurality of appliances in the form of slotted brackets is provided for cooperating with an archwire to apply corrective forces to a patient's teeth on which the brackets are mounted. Another aspect of the invention concerns a method of making plastic orthodontic appliances suitable for mechanical bonding. The method includes molding a plastic orthodontic appliance having projections with undeformed outer ends or tips and subsequently bombarding the tips of the projections with particles impinged thereon, for example as by peening, to widen the outer extremities of the projections to form the undercuts. In the preferred embodiment of the method, ANSI no. 2 glass beads are fluidized and blown in an air stream onto the tips of the projections to widen and fracture the end regions of the projections, providing the surface with a characteristically peened texture, preferably one that includes fractures into the end regions.

15 Claims, 4 Drawing Sheets

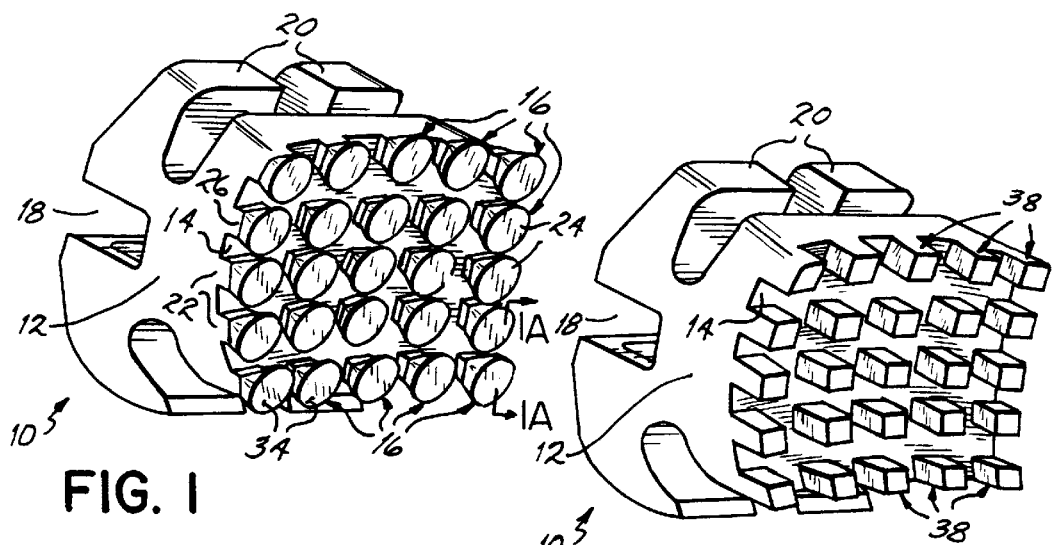
FIG. 1
FIG. 1B
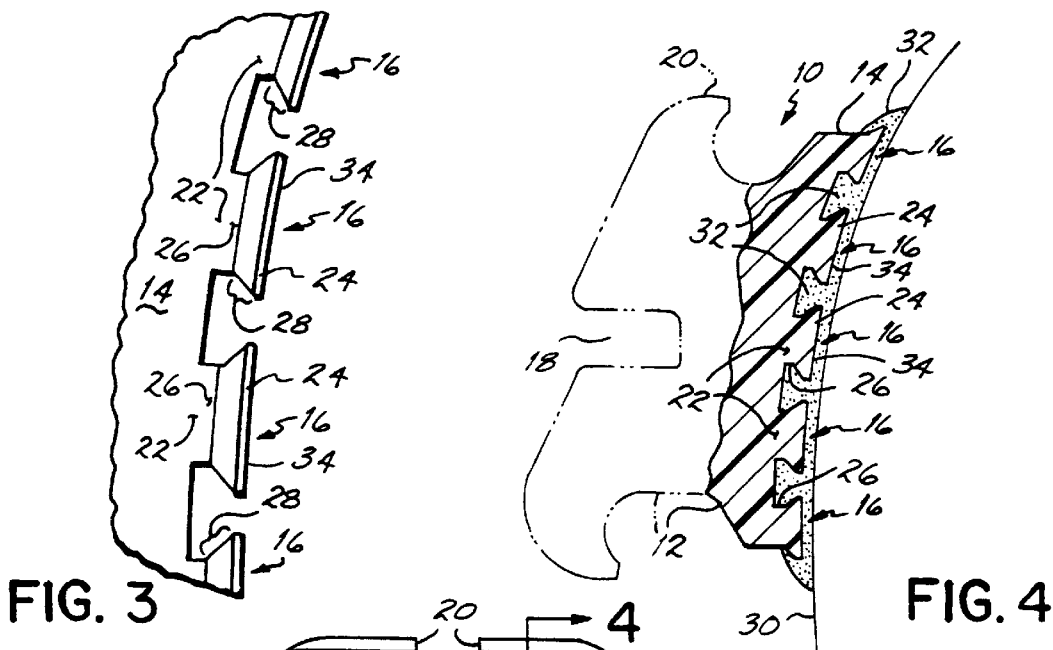
FIG. 3
FIG. 4
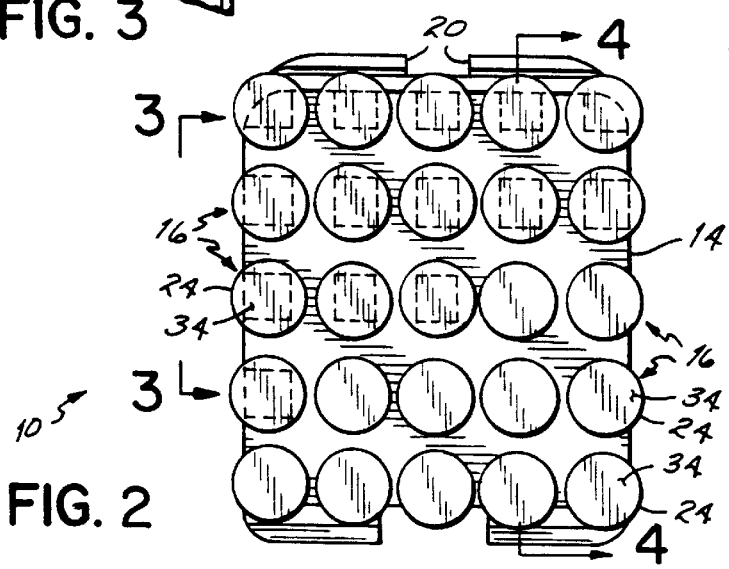
FIG. 2

PLASTIC ORTHODONTIC APPLIANCE HAVING MECHANICAL BONDING BASE AND METHOD OF MAKING SAME

This application is related to the commonly assigned and copending U.S. patent application Ser. No. 09/181,154, which is a continuation of U.S. patent application Ser. No. 08/859,484, filed May 5, 1997, now U.S. Pat. No. 5,829,973, which is a continuation of U.S. patent application Ser. No. 08/692,923, filed Jul. 31, 1996, now abandoned, which is a division of U.S. patent application Ser. No. 08/391,663, filed Feb. 21, 1995, now U.S. Pat. No. 5,622,494, all hereby expressly incorporated by reference herein.

FIELD OF THE INVENTION

This invention is directed to orthodontic appliances, and more particularly, to a plastic orthodontic appliance having structure on an appliance base to facilitate the mechanical bonding of the appliance to a tooth surface with an adhesive.

BACKGROUND OF THE INVENTION

In the field of orthodontics, it is known to adhere orthodontic appliances, such as brackets, buccal tubes and the like, directly to teeth. Typically, this is accomplished by chemically bonding an appliance to a tooth surface using an adhesive. If desired, the bonding surface area of the appliance may be roughened in order to increase the surface area of the appliance in contact with the adhesive, thereby enhancing the chemical bond. Direct bonding also may be accomplished by using a metal appliance having undercuts for forming a mechanical bond with the adhesive.

U.S. Pat. No. 5,267,854 to Schmitt teaches a metal injection molded orthodontic bracket including a plurality of raised posts extending bucco-lingually from a tooth abutting surface. Each post includes a root section having a base integrally formed with the tooth abutting surface and an apex section bucco-lingually extending from the root section. The apex section terminates in a sharp, continuous parameter edge that was originally smaller in all directions than the root section. However, in accordance with the Schmitt patent, further cold working of the parameter edges occurs such that each edge is worked at ambient temperatures into a mushroom-shaped button having a worked edge larger in all directions than its associated root section and an eave capable of mechanically bonding with an adhesive.

U.S. Pat. No. 4,661,059 to Kanno features a metal orthodontic bracket which has a base surface provided with a plurality of orthogonal grooves formed by a cutting machine having a plurality of rotatable thin circular cutter blades. The grooves so produced have small fins or flashes at their edges resulting from cutting operations of cutter blades scraping metal matrix at high speed. These small fins are pressed down into the inside of the grooves to form undercuts for the adhesive to provide mechanical bonding of the base to the tooth surface.

Although mechanical bonding provides some advantages over traditional bonding methods, the brackets taught by Schmitt and Kanno have several limitations. For example, both brackets are made of metal and therefore, lack the aesthetic qualities found in plastic or ceramic orthodontic appliances. Furthermore, the mechanical bonding surfaces of the Schmitt and Kanno brackets are formed by cold working the metal at ambient temperature. This cold working process also distorts the metal microstructure of the raised posts used for mechanical bonding.

In addition, the methods used to form the mechanical bonding surfaces are relatively complex and expensive. The Schmitt patent requires the use of a hydraulically activated metal coining die array to cold work the posts, with one die for each post, and with each die having a partially spherical concave mushroom forming cavity in the tip. Such die arrays are difficult to make, expensive to manufacture, and difficult to use. Kanno teaches the use of a cutting machine to form the posts in the bracket base, which leads to a significant amount of wasted metal. Also, the raised posts of the Schmitt bracket must be originally molded with an apex section narrower than the root section in order to remove the metallic bracket from the mold without significant risk of peg breakage. This tapering results in less metal being available at the apex to form the mushroom-shaped button and corresponding eave required for mechanical bonding. Furthermore, the extremely fine fins or flashes of the Kanno bracket formed by the cutting process must be pressed downward in order to form the mechanical bonding surfaces and are subject to stress and fracture in this process.

In the related patents and applications referred to above, the bracket bases are formed of plastic having arrays of pegs projecting from their bases, with the outer ends or tips of the pegs having mushroom shaped heads that present overhangs which facilitate mechanical bonding of the bases to the surfaces of teeth with adhesive. The heads are formed by heat softening the peg tips and, while softened, applying a force to the tips in a direction toward the base, deforming the tips into mushroom-shaped heads.

Therefore, it would be beneficial to have an improved method of deforming peg tips of projections on orthodontic appliance bases into mushroom-shaped heads without the need to use heated platens to soften the projections to facilitate their deformation or to use expensive cold working coining dies in order to make an orthodontic appliance capable of being mechanically bonded to a tooth, in which the appliance is made of an aesthetically pleasing material.

SUMMARY OF THE INVENTION

This invention is directed to a process for forming an orthodontic appliance, and the appliance so formed, having projecting structure extending from an appliance base which is adapted to mechanically bond to a tooth surface with an adhesive. The process includes forming, by injection molding for example, a thermoplastic orthodontic appliance having a base from which projecting structure, such as ridges, posts or the like, outwardly extends. The projecting structure has an inner extremity and an outer extremity, with the inner extremity being integrally connected to the appliance base. The process further includes the bombarding of the outer extremity, which may be a plurality of discrete outer ends if posts are used, with an airborne stream of solid particles, to deform the projecting structure and provide undercuts proximate the outer extremity for facilitating mechanical bonding of the appliance base to a tooth surface.

In the preferred embodiments of the invention, the thermoplastic orthodontic appliance typically is formed of a glass-filled polycarbonate material. The particles which bombard the projecting structure to form the undercuts are preferably round or elongated beads or shot. In the preferred embodiment of the process, round glass beads, ANSI No. 2 in size, are directed in an air stream perpendicularly toward the base of the appliance, against the end surfaces of the outer extremities or tips of the projecting structure. The particles are suspended in air at an appropriate density in a fluidized mixture and are expelled at an appropriate velocity, controlled by regulating supply air pressure, from a nozzle positioned at an appropriate distance from the appliance base so as to impart a momentum to the particles that will impact the end surfaces to produce an optimal deformation of the outer extremities or end regions of the projecting structure. The time during which each point on the base of an appliance is exposed to such a stream of particles is selected to produce the desired degree of post tip deformation and desired tip end surface texture. Specific values for operating parameters in accordance with the preferred embodiment of the invention are given below that produce the desired result for specific equipment, but it should be appreciated that the operating parameters of the method for each system should be adjusted empirically to optimize the deformation process.

The ideal sizes and types of particles used may vary as other parameters vary or where the geometries of the projections and the material of which the projections are made to differ from those set forth in the examples below. For example, the particles may be round or elongated beads or fletchette-like elongated fibers. Such elongated fibers can be pneumatically oriented in an air stream to flow longitudinally with the airstream and impact the projections endwise. The particles may be made of glass or other ceramic material, metals of various types or other materials that will provide various momentums and propelled at differing velocities, as required to produce the desired deformation of the projecting structure end regions or tips.

For the one embodiment of a system that is illustrated and described in detail below, a nozzle is spaced about 2.5 inches above a linear fixture about six inches long that holds about 50 appliances with their bases facing upwardly. Air is supplied to the nozzle at about 28 psi and at a flow rate of approximately 30 standard CFM, carrying approximately 7 or 8 grams per second of ANSI #2 glass beads. The fluidized stream of beads uniformly covers an area of about ⅝ inches in diameter, which scans the 6 inch fixture in two passes of about 10 seconds per pass. The beads impinging upon the bracket bases have a velocity sufficient to produce a pressure on the projections of preferably at least 50 to, and not more than, about 95 to 100 psi on a flat surface in the position that the holders of the brackets would occupy during processing. In the preferred embodiment, 7.35 grams/second of beads has been determined satisfactory and is preferred, applied used to produce pressure of between 60 and 84 psi, or 72.1+/−11.6 psi. A general flow of air past the fixtures and out the exhaust to a bead sorting and reclaiming device is maintained at about 900 CFM.

The preferred appliance of the present invention is produced according to the method of the invention. Such appliance preferably includes structure projecting from a base of the appliance and increasing in transverse dimension in their outer extremities or end regions in the direction toward their outer ends, preferably by more than 25%, for example by about 40% to 50%. The outer or end surfaces of the tips of the projections are imparted with certain effects that are characteristic of a peening process, that is a process by which the end surfaces of the tips of the projections are bombarded with a plurality of particles which impact upon the end surfaces. The impacts locally dent and compress a plurality of regions on the end surfaces of the projections to effectively widen the outer extremities or end regions of the projections and/or considerably fracture or shatter the end surfaces to various depths in the longitudinal direction into the end regions of the pegs. The fractures and dents cause the end regions to widen into mushroom-shaped heads which form undercuts. The fractures also cause the ends of the projecting structure to take on a brush like texture and present a substantially roughened surface having greater surface area for contact with adhesive than the area provided by deformed, softened plastic and cold worked metal appliance base projections, thereby enhancing the strength of the interface between the appliance base and the adhesive and accordingly the bond between the appliance and the tooth.

The partial bombardment with particles impinged on the end surfaces of the projections applies force to the outer extremity or end regions of the projecting structure in a direction along the length thereof toward the base, thereby slightly compressing or shortening the projecting structure. This force application step deforms the outer extremity of the projecting structure into a substantially mushroom-shaped configuration to thereby provide undercuts proximate the outer extremity. In a preferred form of the invention, the projecting structure is compressed in the range of about 0.001 inch to about 0.004 inch in length.

The projecting structure itself may be one, or several, of many different shapes and alignments extending from the appliance. For example, a solid post or posts, a hollow tubular post or posts, a bristle or bristles, a ridge or ridges, or combinations thereof, may be used. If a plurality of posts is used, preferably, each of the posts has a generally square shaped cross-sectional area along its entire length prior to deformation of the outer ends thereof. A cross-sectional dimension of about 0.015 inch by about 0.015 inch is preferable. In the preferred embodiment, the posts are located on an imaginary grid and are spaced such that the center-to-center distance from one post center to an adjacent post center is approximately 0.030 inch. Furthermore, after deformation, the posts have a length of from about 0.005 inch to about 0.010 inch.

When the orthodontic appliance is formed as an orthodontic bracket, the plastic may include reinforcing glass fibers and may have a reinforcing insert proximate an archwire slot.

The inventive orthodontic appliance and method discussed above offer several benefits and advantages. For example, the appliance offers the strength of a mechanical bonding surface, as well as increased surface area for chemical bonding, in an aesthetically pleasing orthodontic appliance. Whereas conventional mechanical bonding brackets are formed of a metal such as stainless steel, the inventive appliance is formed of an aesthetically pleasing thermoplastic such as polycarbonate, which typically has a translucent tooth-like appearance. Furthermore, the method for forming the appliance is relatively simple and inexpensive in comparison with the cold working methods presently used on metal brackets and the heat softening and plastic deforming methods used on thermoplastic brackets. Also, the particle bombardment peening of the projecting structure tips results in a cold working of the ends of the structure which fractures the end regions of the projecting structure and/or dents the end surfaces of the projections so as to distort the microstructure of the raised plastic posts in a beneficial way, maintaining the structural integrity of the plastic material while enabling the adhesive to provide a high bond strength between the appliance and the tooth surface.

These and other objectives and advantages of the present invention will be more readily apparent from the following detailed description of the drawings, in which:

BRIEF DESCRIPTION OF THE DRAWINGS

FIG. 1 is a rear perspective view of an orthodontic bracket according to a preferred embodiment of the invention after the posts have been deformed to provide a mechanical bonding base.

FIG. 1B is a rear perspective view of an orthodontic bracket before the posts have been deformed.

FIG. 2 is a rear view of the orthodontic bracket of FIG. 1.

FIG. 3 is an enlarged view of the deformed posts of the orthodontic bracket of FIG. 2 taken along line 3—3.

FIG. 4 is a partial cross section of FIG. 2 taken along line 4—4, showing the bracket adhered to a tooth surface.

DETAILED DESCRIPTION OF THE INVENTION

Figure 1A:
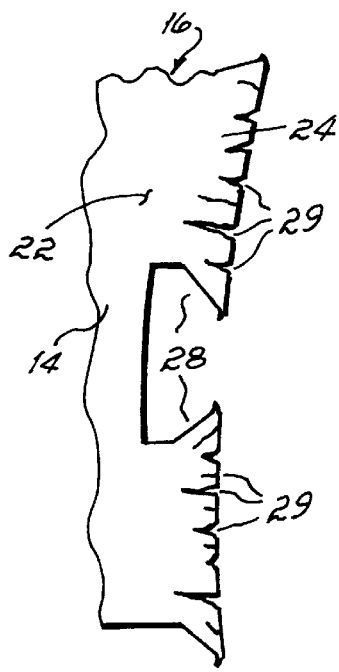
FIG. 1A is a cross-sectional view of the bracket of FIG. 1 taken along line 1A—1A of FIG. 1.

As used herein, the term "orthodontic appliance" refers to a device which is adhered to a tooth surface and, in the practice of orthodontics, is so adhered in conjunction with moving teeth to or holding teeth in a particular position. Nonlimiting examples include orthodontic brackets, buccal tubes and the like. The term "plastic" as used in the description and claims is meant to include plastic material whether or not reinforced with glass fibers or some other reinforcing material and/or other additives such as fillers, pigments, etc. In addition, the term "projecting structure" refers to any structure which extends outwardly from an orthodontic appliance base and which may be deformed at its outer extremity, thereby forming an undercut proximate the outer extremity which is adapted to form a mechanical bond with an orthodontic adhesive when the adhesive cures. Nonlimiting examples of projecting structure include a solid post or posts, a hollow tubular post or posts, a bristle or bristles, a ridge or ridges, or a combinations thereof. A few more detailed examples include ridges in the form of concentric circles, squares, triangles or rectangles; solid posts or hollow tubular posts or projections in the form of circles, rectangles or triangles; a nonintersecting single continuous ridge such as a spiral or serpentine zig-zag; plural nonintersecting ridges such as a basket-weave pattern, on parallel or randomly aligned ridges; plural or intersecting ridges which intersect to form a grid-like pattern, maze or random orientation; and brush-like bristles.

Referring to FIGS. 1 and 2, a plastic orthodontic bracket 10 according to the principles of the invention includes a body 12 and a bracket base 14, with a plurality of posts 16 extending outwardly from the bracket base 14 in a grid-like pattern. The bracket further includes an archwire slot 18 and a pair of tie wings 20.

As shown in FIG. 3, each of the posts 16 has an inner end 22 integral with the bracket base 14, an outer end 24 and an intermediate section 26 disposed between the inner and outer ends 22, 24. Each post further includes an undercut 28 for forming a mechanical bond with an orthodontic adhesive. Referring to FIG. 4, an orthodontic bracket 10 is shown bonded to a tooth surface 30 using an orthodontic bonding adhesive 32. Typically, an orthodontist will apply the adhesive 32 to the bracket base 14, allowing the adhesive to flow into and fill the open spaces between the posts 16 as well as cover the outer ends 24. The bracket 10 then may be placed on the tooth surface 30, and as the adhesive 32 cures, a chemical bond and a mechanical interlocking bond is formed between the adhesive 32 and the bracket 10 or other orthodontic appliance. A bond is also formed between the adhesive and the tooth surface. The mechanical undercuts 28 in the bracket cause the bracket 10 to more tightly bond to the tooth than a bracket having a smooth bonding surface, thereby enhancing the adhesion of the bracket 10 to a tooth 30. Additionally, the posts 16 increase the surface area of the base 14, enhancing the chemical bonding with the adhesive to the base. Furthermore, it is believed that the bond may be not only similar in strength (shear or tensile force to bond failure at low strain rates) to mesh-based brackets, but also tougher (more impact resistant) than the bond for metal or ceramic brackets, because of the relative flexibility of the posts 16 and the inherent ductility of the plastic material.

As more particularly illustrated in FIG. 1A, each of the posts 16 has the inner end 22 thereof integral with the bracket base 14, with the outer ends 24 having a plurality of longitudinal fractures 29 extending to various depths in the end of the posts 16 thereby causing a brushlike expansion of the tip that increases the transverse cross-section of the region 24 which extends longitudinally from the outer end of the posts 16 a fraction of the total length of the posts 16, which defines a mushroom-shaped head at the outer region of the each projection forming the undercut 28. The fractures will have an average depth of up to 40% or 50% of the length of the projections, with a significant portion of the fractures extending to different depths of from 0.002 inches up to about 0.005 inches into the projections. The tips of the projections will have a characteristically peened character, exhibiting the fractures, or a plurality of dents or other characteristic deformations of a particle bombardment process. The undercut 28 as well as the fractures enhance the formation of a mechanical bond with an orthodontic adhesive.

Figure 6:
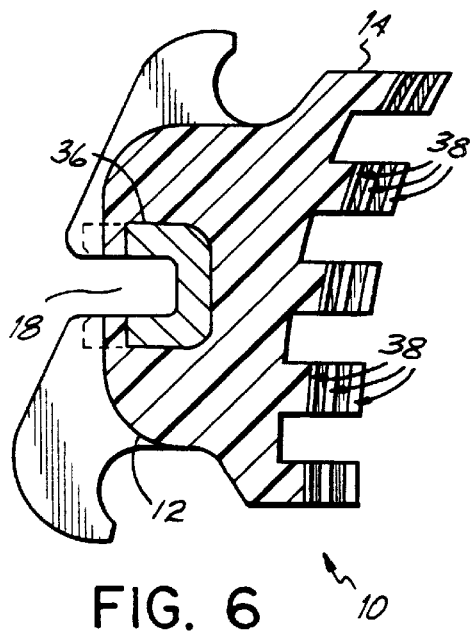
FIG. 6 is a cross-section of the bracket of FIG. 5 taken along line 6—6.
Figure 7:
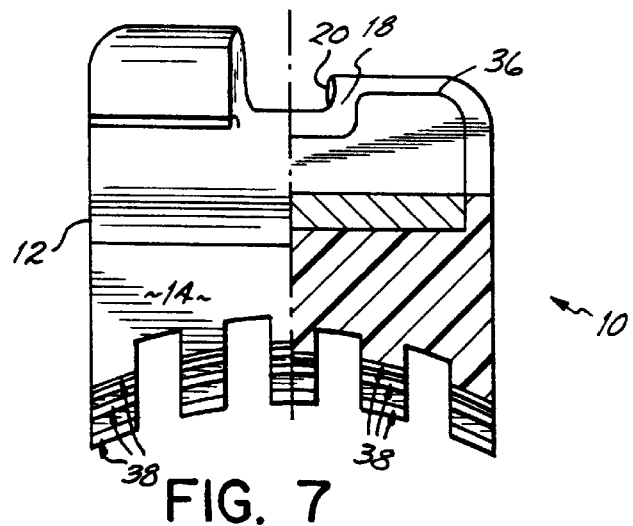
FIG. 7 is a partial cross-section bottom view of the bracket of FIG. 5 taken along line 7—7.

Preferably, the plastic orthodontic appliance is formed of a polycarbonate reinforced with glass fibers as taught in U.S. Pat. No. 5,254,002, which is hereby incorporated in its entirety herein by reference, with the fibers preferably being about 20%–40% by weight. Referring to FIGS. 6 and 7, when the orthodontic appliance is a bracket 10, the bracket 10 preferably includes a metal insert 36 disposed within the archwire slot 18, as taught in the referenced patent.

The preferred embodiment of the orthodontic appliance also has an appliance base with a compound curvature corresponding to the curvature of a tooth surface. Furthermore, as shown in FIGS. 1, 1B, 4, 6 and 7, the outer ends 24 of the posts 16, when viewed in combination, generally follow this same compound curvature, both before and after deformation.

As shown in FIG. 2, a preferred embodiment of the appliance has about 25 posts 16 arranged in a grid-like pattern. Each post has a square shaped cross-sectional area through its inner end 22 and intermediate section 26, with dimensions of about 0.015 inch×0.015 in. In addition, referring to FIG. 3, each broadened outer end 24 has a length of about 0.005 in. to about 0.010 in. from the inner end 22 to the tooth facing surface 34 of the broadened outer end 24. As further seen in FIG. 2, the spacing between post inner ends 22 is similar to the cross-sectional dimensions of the inner ends 22 themselves, ranging from about 0.010 in. to about 0.020 in.

Regardless of the particular projecting structure employed, the space between adjacent portions of the deformed outer extremity of the projecting structure (for example, between adjacent broadened outer ends of an embodiment using discrete posts) must be sufficient to permit the adhesive to flow between the deformed adjacent portions into the undercut region below, which is a function of the adhesive viscosity and the method of application of the adhesive to the base.

In another embodiment (not shown) the appliance base has a centrally located area which is free of posts. This open area may be formed with an identifying mark, such as a letter or number, to assist in the identification of the appliance. The portions of the appliance base immediately adjacent to the open area may have partial posts, such as posts with smaller cross-sectional dimensions. While this embodiment slightly reduces the number of posts available for mechanical bonding, it still is able to form a strong mechanical interlock with an adhesive.

Typically, the orthodontic appliance is formed in a multi-step process. As shown best in FIG. 1B, as well as in FIGS. 6 and 7, a preferred bracket 10 or other appliance is molded having undeformed posts 38, and the broadened outer ends of the posts are formed in a secondary operation. The intermediate-stage appliance (having undeformed posts or other projecting structure) may be formed using a conventional thermoplastic molding technique as is taught by U.S. Pat. No. 5,254,002, preferably by injection molding.

Different molds may be used to achieve the desired sizing and distribution of undeformed posts or other projecting structure, and when an appliance having a plurality of posts is to be formed, preferably the mold is shaped so as to produce an appliance having post size and distribution as discussed above. Furthermore, the portion of the appliance mold used to make the undeformed posts or other projecting structure preferably has no draft (i.e., the walls of the cavities in the mold corresponding to the posts may be vertical as opposed to being tapered). This ability to have vertical walls in the mold generally is not possible for a metal bracket having mechanical bonding posts because the greenware (molded metal bracket before sintering) is very fragile, and without tapered side walls in the mold that produce posts which have smaller cross-sectional dimensions toward their outer ends, some posts likely would break as the metal bracket is removed from the mold cavity. However, because the appliances of the present invention are formed of plastic, a mold having vertical side walls may be used without significant risk of projecting structure breakage. This feature provides enhanced strength to the posts or other projecting structure during both initial formation and subsequent broadening of the outer extremity. The feature also produces projecting structure having more material at its outer extremity relative to molded metal posts, thereby enhancing the undercuts and mechanical bonding between the undercuts and the bonding adhesive.

While a preferred embodiment has been described in detail in the form of an orthodontic appliance having a projecting structure comprising a plurality of discrete posts, numerous alternative embodiments of the projecting structure may be provided, a few of examples of which are shown in FIGS. 10A–10F.

Figure 10A:
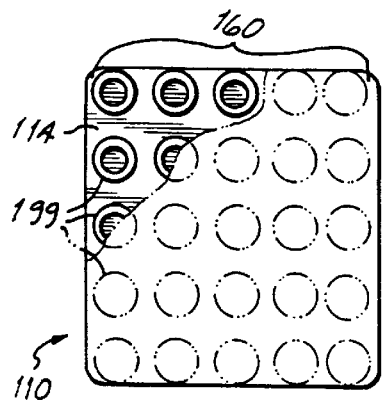
FIGS. 10A, 10B and 10D–10F are rear views of orthodontic appliances, illustrating a few alternate embodiments of the projecting structure in an undeformed state.
Figure 10B:
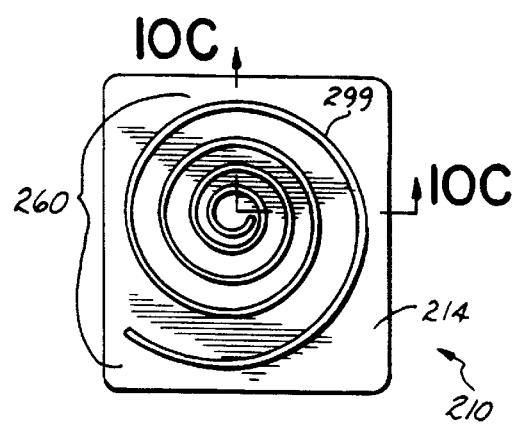
Figure 10C:
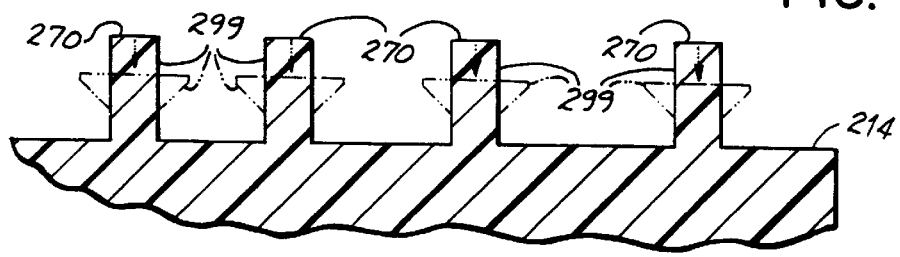
FIG. 10C is a partial cross-section of FIG. 10B taken along line 10B—10B, illustrating the projecting structure in both undeformed and deformed (shown in phantom) states.
Figure 10D:
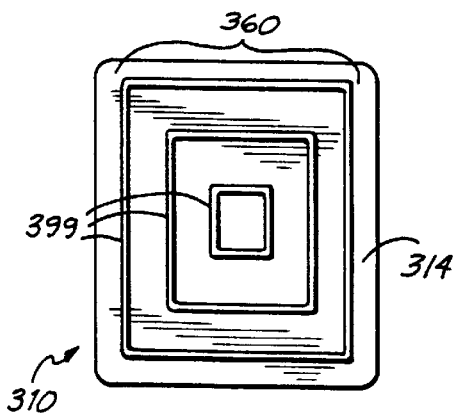
Figure 10E:
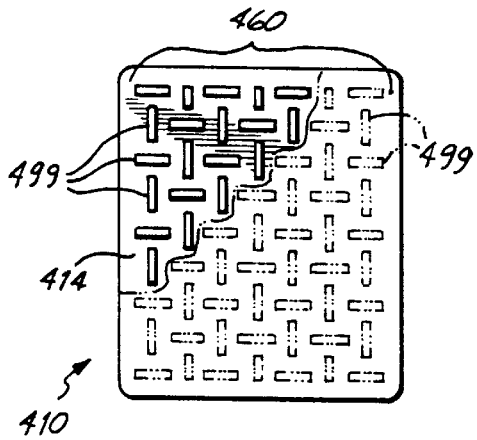
Figure 10F:
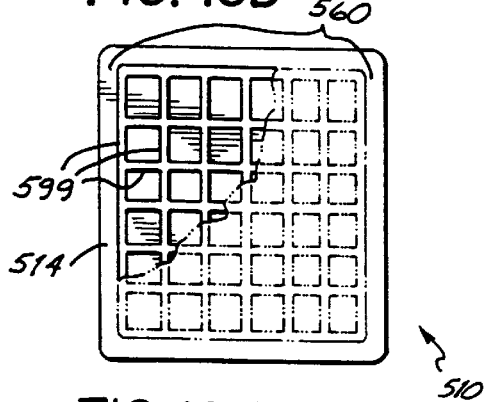

Referring to FIG. 10A, the orthodontic appliance 110 may have projecting structure 160 extending outwardly from the appliance base 114 which is a plurality of discrete, circular, hollow tubular posts or projections 199. FIG. 10B illustrates an appliance 210 having a projecting structure 260 in the form of a spiral-like ridge 299 extending from the appliance base 214. FIG. 10C is a partial cross-section of the spiral-like ridge 299 of FIG. 10B illustrating the projecting structure 260 in an undeformed and deformed (shown in phantom) state. The outer extremity 270 of the projecting structure 260 also is clearly visible. In FIG. 10D, the appliance 310 has a projecting structure 360 which is a series of concentric rectangles 399 extending outwardly from the appliance base 314, while in FIG. 10E the appliance 410 has a series of discrete nonintersecting ridges 499 aligned in a basket-weave pattern which extend outward from the appliance base 414. The appliance 510 shown in FIG. 10F includes a projecting structure 560 which is a series of intersecting ridges 599 arranged in a grid-like pattern and extending outwardly from the appliance base 514.

Figure 9:
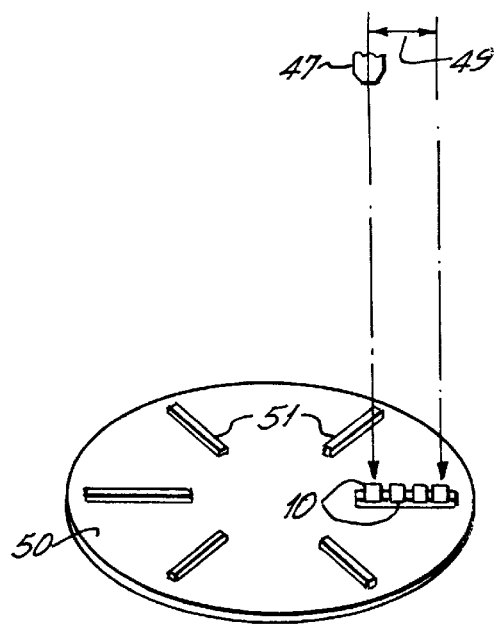
FIG. 9 is a cross-sectional view of the deforming station of the apparatus shown in FIG. 8.
Figure 8:
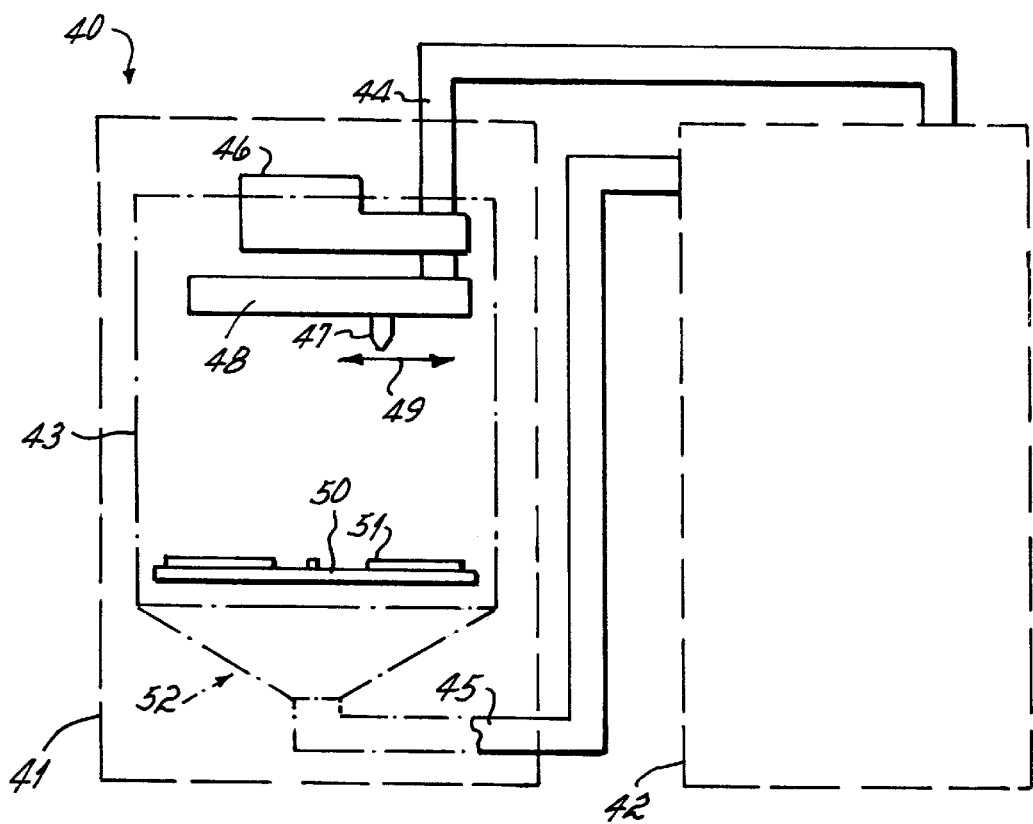
FIG. 8 is a perspective view of an appliance forming apparatus including a projecting-structure deforming station for use in a preferred embodiment of the method of forming an orthodontic appliance of the present invention.
Figure 5:
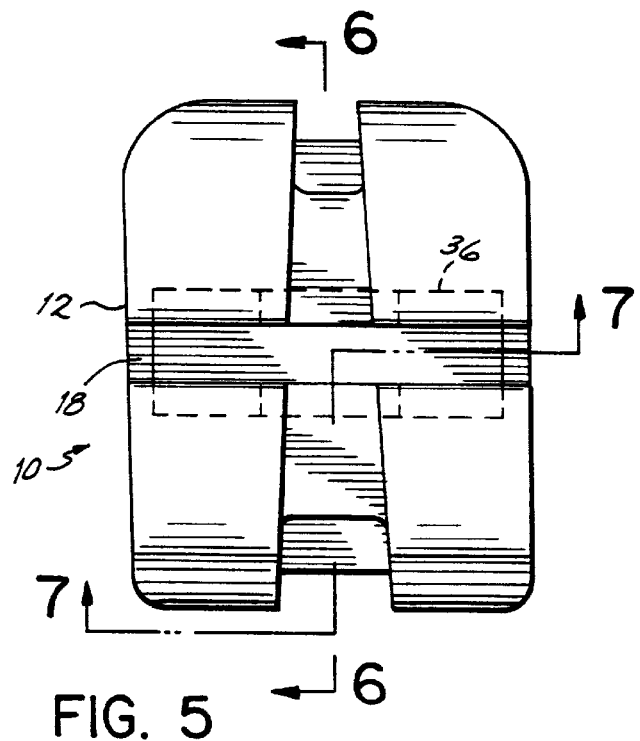
FIG. 5 is a front view of the orthodontic bracket of FIG. 1B.

In the preferred method of forming the orthodontic appliance, the posts or other projecting structure are deformed using a projecting-structure deforming apparatus 40 that includes a deforming station 41 and a particle reclaiming and recycling station 42, as shown in FIGS. 8 and 9. The deforming station 41 preferably includes a commercially available shot-peen or sandblast treating apparatus, such as a Model A 200-1 bead blasting cabinet manufactured by Zero Products, a division of Clemco Industries Corp. The deforming station 41 has a sealed chamber enclosure 43 having an air inlet 44 stack on the top thereof and an exhaust duct 45 on the bottom which connects to a media reclaiming and classification system. Connected to the inlet 44 is a particle feeder and metering valve system and regulator 46 which outputs a fluidized stream of particles, in the preferred embodiment ANSI No. 2 spherical glass beads, to a nozzle 47. Particles that are of a size that is equal to or slightly larger than the spaces between the posts are avoided, so that effective peening of the tips of the posts occurs without having beads remain stuck between the posts. The nozzle 47 is downwardly directed and is moveable by way of a moveable mounting structure 48 so as to reciprocate along a straight path 49 of approximately 6 inches in length.

Located in a horizontal plane approximately 2.5 inches below the nozzle 47 is a 30 inch diameter rotatable urethane coated turntable 50, which is controlled to index through six equally spaced angular orientations to sequentially present each of six linear workpiece holders 51 correspondingly mounted at six angular positions on the turntable 50 below and in-line with the path 49 of the nozzle 47. The nozzle 47 is configured to eject a column of airborne glass beads approximately ⅝ inch in diameter onto the a workpiece holder 51 and to move radially across the turntable 50 to scan lengthwise the holder 51 that is positioned below the path 49. The scan proceeds from the radially outer end of the holder 51, as mounted on the turntable 50, to the inner end and back to the outer end to cover the workpiece holder with a uniform stream of airborne beads throughout its length in two passes. While such scanning may take a total of up to about one minute, in the preferred embodiment, two 6 inch passes of the ⅝ beam are carried out at about 10 seconds per each 6-inch pass, with the nozzle spaced at about 2.5 inches above the holder 51. The airborne bead stream is emitted from the nozzle at a pressure of approximately 28 pounds per square inch (psi) with approximately 30 standard CFM of air supplied to the nozzle. This amount of air carries in the general order of magnitude of 7 or 8 grams of the No. 2 glass beads per second. 7.35 grams per second has been determined to be particularly satisfactory.

On each workpiece holder 51 are mounted a plurality of about fifty plastic orthodontic brackets 10 having preformed and undeformed pegs thereon as illustrated in FIGS. 1B, 6 and 7, with the bases facing upwardly and the pegs projecting upwardly toward the nozzle 47. An exhaust system 52 is provided to remove spent beads from the turntable 50 and to exhaust them to the reclaiming station 42. The exhausted and reclaiming air is moved at a flow rate of about 900 CFM. The reclaiming station 42 also includes a Zero model RHP-2L dust collection system.

With the deforming station 41, it is found that optimal deformation of the posts 16 occurs when certain process parameters are used, such as by having the beads impinge upon the bracket bases with a momentum or velocity such as to produce a pressure of between 50 to 95 psi on a flat test surface occupying the normal position that the brackets would occupy. This pressure is preferably measured by the use of pressure measurement film, such as Fuji PRESCALE™ film manufactured by Fujifilm of Japan, available from Itochu Canada Ltée OF Montreal Canada. The pressure measurement is performed film by adhesively applying a strip of the film to the surface of the turntable 50 in the position normally occupied by the workpiece holders 51 and then directing the stream of beads onto the film by operating the apparatus in the same way as if processing bracket bases. The impinging of the beads onto the film alters microcapsules of color forming material in the film in relation to the pressure applied by the beads to the film. Film reading devices are available with the Fuji PRESCALE system to interpret the color changes in the film to accurate pressure values.

In the preferred embodiment, 7.35 grams/second of beads is used to produce this pressure of between 60 and 84 psi. A particularly satisfactory setting produced a pressure on the tape, applied onto a metal surface and directed face the nozzle, of 72.1+/−11.6 psi. A general flow of air past the fixtures and out the exhaust to a bead sorting and reclaiming device is maintained at about 900 CFM. These parameters and those set forth above have been found to produce an optimal total particle momentum for producing the desired deformation of the tips of the posts.

The reclaiming station 42 filters the spent beads from the airstream and separates broken beads from the undamaged beads. The broken beads are removed from the system and the undamaged beads are recycled into the feeder 46 at the input of the deforming station 41. New beads are added to the system to replace the damaged beads that are extracted at the reclaiming station 42 to replenish the bead supply to the deforming station 41.

It is to be understood that various changes and modifications may be made from the preferred embodiments discussed above without departing from the scope of the present invention, which is established by the following claims and equivalents thereof.

What is claimed is:

1. A method of forming an orthodontic appliance having projecting structure extending from an appliance base which is adapted to mechanically bond to a tooth surface with an adhesive, comprising the steps of:

forming a plastic orthodontic appliance base from which outwardly extends a plurality of projections each having an inner extremity integrally connected to said appliance base, an outer extremity terminating in a free end and a generally uniform cross section from the inner extremity to the free end; then deforming the outer extremities of the projections by impinging a stream of particles toward the base and bombarding the free ends of the projections therewith to widen the projections to increase the cross section adjacent the free ends and thereby form undercuts proximate the outer extremities of the projections.

2. A method of forming an orthodontic appliance having projecting structure extending from an appliance base which is adapted to mechanically bond to a tooth surface with an adhesive, comprising the steps of:

forming a plastic orthodontic appliance base from which outwardly extends a plurality of projections each having an inner extremity integrally connected to said appliance base and an outer extremity terminating in a free end, the projections each having a generally uniform cross section throughout its length; then deforming the projections by peening the free ends thereof to shorten and widen the projections and increase the cross section of the outer extremity and the free end and thereby form undercuts at the outer extremities of the projections.

3. The method of claim 1 or claim 2 wherein the deforming step includes:

blowing a stream of air-borne particles toward the base and bombarding the free ends therewith.

4. The method of claim 3 wherein the blowing step includes the step of blowing a stream of airborne glass beads toward the base and bombarding the free ends therewith.

5. The method of claim 4 wherein the blowing step includes the step of blowing ANSI no. 2 sized glass beads toward the base and bombarding the free ends therewith.

6. The method of claim 5 wherein the blowing step includes the step of blowing the glass beads in an air stream at a density of about 7.35 grams per second in air flowing at a rate of about 30 SCFM and directed to produce a pressure of between about 50 and 100 psi on a surface in the position of the free ends of the projections.

7. The method of claim 5 wherein the blowing step includes the step of blowing the glass beads in an air stream at a density of about 7.35 grams per second in air flowing at a rate of about 30 SCFM.

8. The method of claim 5 wherein the blowing step includes the step of blowing the glass beads in an air stream to produce a pressure of between about 50 and 100 psi on a surface in the position of the free ends of the projections.

9. The method of claim 5 wherein the blowing step includes the step of blowing the glass beads in an air stream to produce a pressure of between about 60 and 85 psi on a surface in the position of the free ends of the projections.

10. The method of claim 5 wherein the blowing step includes the step of blowing the glass beads in an air stream to produce a pressure of between about 72 psi on a surface in the position of the free ends of the projections.

11. A method of forming an orthodontic appliance having projecting structure extending from an appliance base which is adapted to mechanically bond to a tooth surface with an adhesive, comprising the steps of:

forming a plastic orthodontic appliance base from which outwardly extends a plurality of projections each having an inner extremity integrally connected to said appliance base and an outer extremity terminating in a free end;

impinging a stream of particles to produce a pressure on a strip of pressure measurement tape applied on a flat surface in the position where the appliance base would be situated and then mounting the appliance base in said position; and then deforming the outer extremities of the projections by impinging the stream of particles toward the base and bombarding the free ends of the projections therewith to form undercuts proximate the outer extremities of the projections.

12. A method of forming an orthodontic appliance having projecting structure extending from an appliance base which is adapted to mechanically bond to a tooth surface with an adhesive, comprising the steps of:

forming a plastic orthodontic appliance base from which outwardly extends a plurality of projections each having an inner extremity integrally connected to said appliance base and an outer extremity terminating in a free end;

deforming the outer extremities of the projections by impinging a stream of particles toward the base and bombarding the free ends of the projections with particles having a size, shape and momentum effective to peen the free ends of the projections, and widen the outer extremities of the projections to form undercuts proximate the outer extremities of the projections.

13. A method of forming an orthodontic appliance having projecting structure extending from an appliance base which is adapted to mechanically bond to a tooth surface with an adhesive, comprising the steps of:

forming a plastic orthodontic appliance base from which outwardly extends a plurality of projections each having an inner extremity integrally connected to said appliance base and an outer extremity terminating in a free end;

deforming the outer extremities of the projections by impinging a stream of particles toward the base and bombarding the free ends of the projections with particles having a size, shape and momentum effective to peen the free ends of the projections, and widen the outer extremities of the projections to form undercuts proximate the outer extremities of the projections and a plurality of longitudinal fractures in the free ends of the projections to differing depths into outer extremities of the projections.

14. An orthodontic appliance produced by the method of claim 13.

15. An orthodontic appliance, comprising:

a plastic orthodontic appliance having an appliance base and a plurality of projections structure extending outwardly from the appliance base;

the projections each having an inner extremity integrally connected to the appliance base, an outer extremity and an intermediate section between the inner and outer extremities, each outer extremity terminating in a free end;

the cross-sectional area of the outer extremity being greater than the cross-sectional area of the intermediate section, thereby forming undercuts in the projections to facilitate mechanically bonding the orthodontic appliance to a tooth surface with an adhesive;

the free ends having a peened surface that includes a plurality of fractures extending therefrom longitudinally into the outer extremities of the projections.

* * * * *

UNITED STATES PATENT AND TRADEMARK OFFICE
CERTIFICATE OF CORRECTION

PATENT NO.   : 6,190,165 B1
DATED        : February 20, 2001
INVENTOR(S)  : Andreiko et al.

It is certified that error appears in the above-identified patent and that said Letters Patent is hereby corrected as shown below:

Column 2,
Line 22, reads "mushroom shaped" and should read -- mushroom-shaped --.

Column 3,
Line 17, reads "are made to differ from" and should read -- are made, differ from --.
Line 21, reads "airstream" and should read -- air stream --.
Line 33, reads "#2" and should read -- No. 2 --.
Line 34, reads "inches" and should read -- inch --.

Column 5,
Line 13, reads "cross-section" and should read -- cross section --.
Line 15, reads "cross-section" and should read -- cross section --.
Line 50, reads "a combination thereof" and should read -- combinations thereof --.

Column 6,
Line 11, reads "bond is formed between" and should read -- bond are formed between --.

Signed and Sealed this

Twenty-seventh Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,190,165 B1
DATED           : February 20, 2001
INVENTOR(S)     : Andreiko et al.

It is certified that error appears in the above-identified patent and that said Letters Patent is hereby corrected as shown below:

Column 2,
Line 22, reads "mushroom shaped" and should read -- mushroom-shaped --.

Column 3,
Line 17, reads "are made to differ from" and should read -- are made, differ from --.
Line 21, reads "airstream" and should read -- air stream --.
Line 33, reads "#2" and should read -- No. 2 --.
Line 34, reads "inches" and should read -- inch --.

Column 5,
Line 13, reads "cross-section" and should read -- cross section --.
Line 15, reads "cross-section" and should read -- cross section --.
Line 50, reads "a combination thereof" and should read -- combinations thereof --.

Column 6,
Line 11, reads "bond is formed between" and should read -- bond are formed between --.
Lines 30 and 32, reads "end of the posts" and should read -- ends of the posts --.
Line 31, reads "cross-section" and should read -- cross section --.
Line 35, reads "region of the each" and should read -- region of each --.
Lines 38 and 39, reads "inches" and should read -- inch --.

Column 8,
Line 7, reads "cross-section" and should read -- cross section --.
Line 52, reads "onto the a workpiece" and should read -- onto the workpiece --.
Line 61, reads "5/8 beam" and should read -- 5/8 inch beam --.

Column 9,
Line 22, reads "OF Montreal" and should read -- of Montreal --.
Line 23, reads "is performed film by" and should read -- is performed by --.
Line 30, reads "PRESCALE" and should read -- PRESCALE$^{TM}$ --.
Line 37, reads "directed face the nozzle" and should read -- directed to face the nozzle --.

UNITED STATES PATENT AND TRADEMARK OFFICE
CERTIFICATE OF CORRECTION

PATENT NO.    : 6,190,165 B1
DATED         : February 20, 2001
INVENTOR(S)   : Andreiko et al.

It is certified that error appears in the above-identified patent and that said Letters Patent is hereby corrected as shown below:

Column 10,
Line 24, reads "air-borne" and should read -- airborne --.
Line 30, reads "no. 2" and should read -- No. 2 --.
Line 52, reads "pressure of between about 72 psi" and should read -- pressure of 72 psi --.

This certificate supersedes Certificate of Correction issued May 27, 2003.

Signed and Sealed this

Ninth Day of December, 2003

JAMES E. ROGAN
*Director of the United States Patent and Trademark Office*